United States Patent
Schmid

(10) Patent No.: US 9,164,085 B2
(45) Date of Patent: Oct. 20, 2015

(54) TEST STRIP FOR THE DETECTION OF EQUOL

(75) Inventor: Juerg Daniel Schmid, Zurich (CH)

(73) Assignee: System Biologie AG, Wollerau (CH)

( * ) Notice: Subject to any disclaimer, the term of this patent is extended or adjusted under 35 U.S.C. 154(b) by 225 days.

(21) Appl. No.: 13/581,864

(22) PCT Filed: Feb. 25, 2011

(86) PCT No.: PCT/EP2011/000919
§ 371 (c)(1),
(2), (4) Date: Nov. 8, 2012

(87) PCT Pub. No.: WO2011/107238
PCT Pub. Date: Sep. 9, 2011

(65) Prior Publication Data
US 2013/0071937 A1 Mar. 21, 2013

(30) Foreign Application Priority Data
Mar. 1, 2010 (EP) .................................. 10155044

(51) Int. Cl.
*G01N 21/78* (2006.01)
*G01N 33/52* (2006.01)

(52) U.S. Cl.
CPC ....... *G01N 33/52* (2013.01); *Y10T 436/142222* (2015.01)

(58) Field of Classification Search
USPC ............. 422/425–430; 436/93, 131, 166, 169
See application file for complete search history.

(56) References Cited

U.S. PATENT DOCUMENTS

| | | | | |
|---|---|---|---|---|
| 3,001,950 A * | 9/1961 | Hopper | ............................ | 436/71 |
| 3,397,964 A * | 8/1968 | Zall | ................................. | 436/78 |
| 4,119,405 A * | 10/1978 | Lam | ............................... | 436/169 |
| 4,247,297 A * | 1/1981 | Berti et al. | ..................... | 436/169 |
| 4,251,222 A * | 2/1981 | White | ............................... | 436/66 |
| 4,440,724 A * | 4/1984 | Tabb et al. | ..................... | 422/420 |
| 4,797,357 A * | 1/1989 | Mura et al. | ...................... | 435/34 |
| 5,344,759 A * | 9/1994 | Laszlo et al. | ................. | 435/7.32 |
| 5,756,362 A * | 5/1998 | Durst et al. | .................... | 436/518 |
| 6,248,593 B1 * | 6/2001 | Esswein et al. | .................. | 436/77 |
| 6,420,181 B1 * | 7/2002 | Novak | ........................... | 436/104 |
| 2002/0182742 A1 * | 12/2002 | Takagi et al. | ................. | 436/163 |
| 2010/0297775 A1 * | 11/2010 | Green | ............................. | 436/93 |

FOREIGN PATENT DOCUMENTS

| JP | 2006-242602 | | 9/2006 |
|---|---|---|---|
| JP | 2010-169507 A | | 8/2010 |
| RU | 1797020 | * | 2/1993 |

OTHER PUBLICATIONS

Setchell, K. D. R. et al, Jouranl of Nutrition 2006, 136, 2188-2193.*
Dolinsek, F. et al, Analyst 1975, 100, 884-890.*
English language abstract of JP2010-169507A.
Bennetau-Pelissero et al. "ELISA as a new method to measure genistein and daidzein in food and human fluids," Food Chemistry, vol. 82, pp. 645-658 (2003).
Dirscherl, "Eine einfache Farbreaktion zum Nachwies des im Stutenham vorkommenden Equols," Hoppe-Seyler's Zeitschrift Fuer Physiologische Chemie, vol. 264, pp. 57-63 (1940).
Patent Abstract of Japan, English Abstract of JP2006-242602, Gifu Prefecture, published Sep. 14, 2006.

* cited by examiner

*Primary Examiner* — Arlen Soderquist
(74) *Attorney, Agent, or Firm* — Sonapat LLC

(57) ABSTRACT

Subject of the invention is a test strip for the detection of equol by a color change. Subject of the invention are also methods for producing the test strip, methods for using the test strip, and uses of the test strip.

8 Claims, 3 Drawing Sheets

NORMAL URINE MIX UNTREATED 2786 / DOT TINCTURED WITH NITRIC ACID SOLUTION

NORMAL URINE MIX UNTREATED 2789 / DOT TINCTURED WITH NITRIC ACID SOLUTION
DROP OF EQUOL SOLUTION IN WATER PATCH I

NORMAL URINE MIX UNTREATED 2790 / DOT TINCTURED WITH NITRIC ACID SOLUTION
DROP OF EQUOL SOLUTION IN WATER PATCH II

US 9,164,085 B2

TEST STRIP FOR THE DETECTION OF EQUOL

This is the U.S. national stage entry of International Application No. PCT/EP2011/000910, filed on Feb. 25, 2011, which claims priority to European Application No. 10155044.0, filed on Mar. 1, 2010.

BACKGROUND OF THE INVENTION

The invention relates to test strips for the detection of equol in aqueous solutions by a color change, and methods and uses relating thereto.

Isoflavones, also referred to as isoflavonoids, are compounds of mostly yellow coloration, which are derivatives of isoflavones and thus flavonoids. Isoflavones are secondary compounds from plants, which, amongst others, play a role in the plants' defence from pathogens. The ground body of isoflavone is found in clover species. Some well-known isoflavones are daidzein, found as a glucoside of daidzin in soy flour, genistein from soy beans and red clover, prunetin from the bark of plum trees, biochanin A from chickpeas and clover, orobol, santal from sandle wood, red wood and other woods and pratensein from fresh red clover. The isoflavone daidzein [4',7-dihydroxyisoflavone; 7-hydroxy-3-(4-hydroxyphenyl)-4H-1-benzopyran-4-one] is found in soy and is part of many foods and dietary supplements.

The isoflavane equol [4',7-dihydroxyisoflavane, 3-(4-hydroxyphenyl)-7-chromanol] is produced in the intestinal flora after consumption of daidzein. It is assumed that the conversion is carried out by streptococci, lactamid acid bacteria and bifido bacteria. Equol is not found in soy or any other plants. Equol is thus part of the group of secondary plant metabolites.

Equol has a mild estrogenic activity (0.1% of the activity of steroid-estrogens) and can bind to the estrogen receptors ERα and ERβ. Many beneficial effects are attributed to equol, for instance a cholesterol reducing effect, an anti-inflammatory effect, positive effects on breast cancer and on physiological changes after menopause. Equol also inhibits DHT production in males due to interactions with the 5α reductase. It is assumed that DHT is a cause in the forming of prostate cancer in males. Other benefits may be the treatment of male pattern baldness, acne and other problems related to DHT.

After the consumption of foods which are rich in daidzein, equol is detectable in blood and urine if a person is capable of producing equol. However, only about a third (Caucasian population) up to half (Japanese population) of humans can produce equol from daidzein. In humans who are capable of producing equol ("equol producers"), the positive effects of a soy-rich diet is more pronounced compared to humans, which are not capable of producing equol.

In order to predict whether an isoflavone-rich diet will be beneficial to a person, it is necessary to determine whether the person is an equol producer. A convenient way of determining this seems to be the detection of equol in urine. In the art, various methods for the detection of equol were described.

WO 2004/009035 A2 relates to various beneficial effects of equol. According to this document, equol is detected after purification by high pressure liquid chromatography (HPLC) by a subsequent analysis by mass spectroscopy. Thus, the method requires complicated and expensive instruments.

Another method for the detection of equol is disclosed in JP 2006-242602. The subject of this document is to provide a simplified method, which does not require HPLC or mass spectroscopy. In order to solve this problem, the inventors provide two methods. A first method is based on the separation of a sample with thin layer chromatography. The method requires a pre-treatment of the sample with enzymes for removing saccharides. After the chromatographic separation of the isoflavones, the plate is developed with a solvent. Subsequently, steps for visualizing the isoflavones are carried out, such as subjecting the plate to a steam of iodine. Although avoiding complicated instruments such as HPLC columns and mass spectrometers, the method is relatively complicated and requires chemicals which cannot be handled easily. A second method requires the cultivation of microorganisms and is also complicated.

The inventors of JP 2006-242602 subsequently published an article with the title "Rapid and Convenient Detection of Urinary Equol by Thin-layer Chromatography"; (J Nutr. Sci. Vitaminol. (Tokyo), 2007, 53(1); 43-7). The method requires the hydrolyzation of urine samples, purification by a reverse phase silica gel column and thin layer chromatography. The method is applied for discriminating equol producers.

Early studies relating to the detection of equol were published in the 1940ies and 1950ies. A method for the color detection of equol in the urine of mares was disclosed by Dirscherl (1940, Physiol. Chem., 264, 57-63). The formation of a red ring at the junction of nitric acid and an aqueous sample solution is indicative of the formation of equol. Other methods are disclosed, in which an equol precipitate is produced and dissolved or in which a solid is produced on a microscopic slide and observed under the microscope. The methods disclosed in this document require the equipment of a chemical laboratory or instruments such as microscopes.

The problems known in the art for the detection of equol thus are relatively complicated. They either require sophisticated and expensive instruments or at least the equipment of a chemical laboratory. Further, potentially dangerous chemicals, such as nitric acid or iodine, are used during the test.

Problem Underlying the Invention

The problem underlying the present invention is to provide a simple and rapid method for the detection of equol. Specifically, the method shall be applicable for a self-test, by which a person can determine whether he/she is an equol producer or not. Thus, the method shall be carried out without sophisticated instruments, especially complicated and expensive instruments such as HPLC, mass spectrometers or microscopes, and without potentially dangerous chemicals, such as nitric acid, iodine or organic solvents. Preferably, the method shall not require a chemical laboratory equipment and trained staff. The method shall be applicable with a low number of process steps. Further, the method shall allow the specific detection of equol, especially in a solution which comprises other isoflavones, or in a complex solution such as urine or a blood fraction. The method shall be sensitive in order to allow a clear distinction between equol producers and non-producers.

Solution of the Invention

The problem underlying the invention is surprisingly solved by test strips, methods and uses as defined by the claims.

Subject of the invention is a test strip for the detection of equol by a color change. According to the invention, the color change is detectable on the surface of the test strip. The color change occurs when the strip is contacted with an aqueous solution comprising equol.

According to the invention, a "test strip" is a simple strip impregnated with at least one reactive agent for analysing an aqueous solution by contacting the aqueous solution with the strip. Preferably, the strip is colorless or has only a weak coloration before having contact with the aqueous solution. In this respect, "colorless" means that the strip is white or has a pale color, depending on the strip carrier material. In a preferred embodiment of the invention, the presence of equol is indicated by a yellow, orange or red color. This means that the color will be predominantly yellowish or reddish, although it might comprise other color components or may be darkened.

Preferably, the color reaction is highly specific. When equol is present in the sample at a significant concentration, a clear and distinctive color change is preferably observed. When equol is not present, the color of the strip does not or essentially not changes, or at least should not change to a color which is indicative of the presence of equol. Specifically, a color change indicative of equol should not be observed when other isoflavones are present, especially those contained in soy, or derivatives produced metabolically after the consumption of soy. Preferably, the color change shall not be observed if the aqueous solution comprises daidzein, daidzin, prunetin, biochanin A orobol, santal and/or protensein or metabolites thereof. Further, the color of the strip shall not be affected by other compounds usually present in urine, such as vitamins, phenols and estrogenic hormones.

In a preferred embodiment of the invention, the aqueous solution is urine, blood or a fraction of urine or blood. The detection of equol in urine is preferred, because, as for similar test strips for the detection of blood sugar etc., the analysis of urine is convenient for the consumer or a laboratory, since it is not necessary to take and fractionate a blood sample. In case equol is detected in blood, it is preferred to use a colorless blood sample, such as blood plasma or serum. According to the invention, it is not necessary to divide the urine into fractions, or to subject the urine to a pre-treatment, for example with enzymes. It is thus preferred that the urine is applied to the test strip without prior purification, fractionation or chemical treatment. However, according to the invention, any body liquid fraction thereof or artificial solution can be examined for the presence of equol.

In a preferred embodiment of the invention, the test strip has a length of 1 to 20 cm and a width of 0.2 to 2 cm. However, the dimensions of the test strip depend on the application. For example, if a test strip is provided exclusively for the detection of equol, it could have the dimensions of a relatively thin rod. On the other hand, the equol test could be combined with other tests on one strip. In this case, the strip might be broader. For example, the strip might comprise another portion for the detection of other urine components, such as daidzein or hormones.

Another subject of the invention is a method for producing a test strip according to at least one of the preceding claims, comprising contacting a carrier with an aqueous impregnating solution comprising nitric acid. Preferably, the nitric acid is concentrated. Concentrated nitric acid has a water content of approximately 64 to 70 weight %. In preferred embodiments, the concentration of nitric acid is between 15% and 70% weight %, preferably between 40 and 70 weight %, or at least 15 weight % or at least 45 weight %. Since the nitric acid always comprises water, the impregnating solution is an aqueous solution. However, the aqueous solution may comprise an organic solvent. As used herein, the term "impregnating solution" refers to an impregnating solution comprising water and optionally additional organic solvent. In principle, the signal strength increases with the nitric acid concentration. However, in case the test strip is developed after contact with the aqueous solution comprising equol, the sensitivity would be increased and the concentration of nitric acid could be lower.

In a preferred embodiment of the invention, the impregnating solution comprises an organic solvent, preferably an aliphatic alcohol, and/or an alkali metal or alkaline earth metal hydroxide. The amount of the components is adjusted in order to obtain the desired signal strength.

In a preferred embodiment of the invention, the organic solvent is toluene, benzene or amyl alcohol. In a preferred embodiment, the aliphatic alcohol is amyl alcohol and/or the metal hydroxide is sodium hydroxide. When adding amyl alcohol, the aqueous solution is rather a suspension or emulsion. As used herein, the term "impregnating solution" also relates to such emulsions or suspensions.

In another preferred embodiment, the impregnating solution comprises nitric acid, a nitrate salt and an organic solvent. For example, the solution comprises between 40 and 80 weight % of nitric acid (with a $HNO_3$ concentration of at least 45 weight %), between 5 and 30 weight % nitrate and between 5 and 40 weight % organic solvent. The nitrate salt is preferably an alkaline or earth alkaline nitrate, preferably sodium nitrate. As the skilled person knows, the same solution can be obtained when producing at least a part of the nitrate in solution from a neutralization reaction of a part of the nitric acid with a base, such as sodium hydroxide.

In a preferred embodiment of the invention, the pH of the solution is below 4, preferably below 2. In a preferred embodiment, the carrier is made of paper, cellulose, nitrocellulose or of organic polymers. The carrier is porous, for example a non-woven or a porous membrane. Carriers, which are stable in the presence of acids, are known in the art.

The test strip may comprise an outer barrier layer, preferably from a water soluble organic polymer, which dissolves rapidly upon contact with water. The barrier layer may confer storage stability to the test strip. For example, the strip can be layered with polyvinyl alcohol (PVOH, PVA). Barrier layers from water dissolving plastics are known in the art. For example, PVOH decomposes, disperses and dissolves within seconds after contact with water. By selecting the film grade, fast dissolution is achieved. A useful barrier material may be pelletized polyvinyl alcohol (available under the trademark "depart" from Environmental Polymers of Irldam UK). Tests with this material have shown that at 23° C. and 50% RH, 30 micron films of polyvinyl alcohol may have oxygen permeation rates ranging from 0.24-1.85 ml per square meter per day, depending on the formulation. Nitrogen permeation rates for film materials are so low that they could not be measured in laboratory tests, suggesting a permeability similar to that of aluminium foil.

It is preferred that the test strip has a long time storage stability, for example for month or years. This can be achieved by using a stable carrier, providing a barrier layer and/or embedding the strip in a sealed packaging, such as a foliage, bag or container. However, it is also possible to provide the test strip as a kit of parts, which comprises an impregnating solution and a carrier. Before using the strip, the user impregnates the carrier with the solution.

In a preferred embodiment of the invention, the method comprises the steps of
(a) providing a carrier and an aqueous impregnating solution comprising nitric acid,
(b) impregnating the carrier with the solution and
(c) drying the carrier.

Another subject of the invention is a method for determining whether an aqueous solution comprises equol, comprising the steps of
(A) contacting the aqueous solution with a test strip of the invention,
(B) detecting the presence or absence of a color change,
(C) deducing from the presence or absence of the color change whether the solution comprises equol.

Another subject of the invention is a method for determining whether a person is an equol producer, comprising the steps of
(i) contacting urine, blood or a fraction thereof from said person with a test strip of any of the preceding claims,
(ii) detecting the presence or absence of a color change,
(iii) deducing from the presence or absence of the color change whether the person is an equol producer.

In the methods of the invention, it is preferred that the presence of equol is determined by a color change to yellow, orange or red. Further, it is preferred that the color change is observed by the eye. It is thus not necessary to use instruments for color detection.

When determining whether a person is an equol producer, it is preferred that the urine or blood is obtained from a patient, which has consumed daidzein or a food or diet comprising daidzein before the test. Preferably, the person has consumed a predetermined quantity of daidzein or a daidzein-comprising product. For example, daidzein comprising products are soy or a soy fraction or soy product, such as the Japanese traditional food natto, or a red clover assay or fraction.

After consumption, equol producers rapidly convert daidzein into equol and excrete it in large amounts. It thus can be monitored directly whether the daidzein is converted into equol or not. The sample, such as urine, should be taken and/or analysed after a sufficient time such that the daidzein is converted to equol. For example, after consumption of daidzein or a daidzein comprising food, a urine sample might be taken and/or analysed after 20 minutes to 10 hours.

The amount of daidzein administered to the individual is chosen such that a clear signal will be observed for an equol producer. The amount of daidzein depends on the selectivity of the specific test strip, but also on the body weight of the individual. For example, between 10 and 2000 mg, preferably between 20 and 1000 mg, between 50 and 500 mg or between 50 and 250 mg daidzein may be administered to the individual before the test, either in pure form or as part of a daizein-comprising product. In other embodiments, the amount of daidzein administered is up to 1000 mg, up to 500 mg or up to 250 mg. The test may also be carried out several times, for example two or three times, after administration of varying amounts of daidzein each. Since the conversion of daidzein to equol is varying between individuals, the assay can also be used to determine whether an individual is a strong equol producer or whether he converts daidzein only partially.

According to the invention, and in contrast to methods known in the art, such as thin layer chromatography, it is not necessary to develop the test strip. The color change occurs without subjecting the test strip, which has been contacted with the aqueous solution, to chemicals for inducing the color change. In contrast, the color change starts after the contact of the test strip with the equol due to a chemical reaction of the test strip with the equol. It is preferred that the color change occurs rapidly after contacting the sample with the test strip, for example within one minute or less than 30 seconds.

Preferably, the color change occurs at an equol concentration which is in the range of physiological concentrations of equol in the urine of equol producers after daidzein consumption. Preferably, the aqueous solution comprises at least 0.5%, or at least 0.1% or at least 0.05% or at least 0.01% equol (w/v).

Subject of the invention is also the use of a test strip of the invention for the detection of equol by a color change. The inventive method is preferably a diagnostic method.

The inventive test strip and methods solve the problem underlying the invention. The test strip allows the detection of equol in a rapid, simple and specific method. The test strip can be used by a person who wants to determine whether he/she is an equol producer. The test strip can also be used by a first person to determine whether a second person is an equol producer or whether a sample from a second person comprises equol. For example, the first person can be laboratory staff, medical staff or other professionals, such as nutrition or diet advisors. The inventive method does not require complicated instruments or specific chemicals besides the test strip.

EXAMPLES

Examples 1 to 4

Preparation of Test Strips

The following standard racemic equol solutions were prepared:

|  | Equol conc. % (w/v) | | | |
| --- | --- | --- | --- | --- |
|  | 0.5 | 0.12 | 0.05 | 0.01 |
| Water, ml | 50 | 50 | 50 | 50 |
| Equol, mg | 250 | 60 | 25 | 5 |

The maximal concentration of equol in water at room temperature is approximately 0.1%. The 0.5% equol solution was prepared in boiling water and used while still hot. After cooling, crystallization of equol occurs.

White filter paper sheets lined into 4 zones were impregnated with solutions with different compositions (table 1). Isoamyl alcohol at higher concentrations is not fully miscible with water and yields heterogeneous emulsions. After drying of impregnated paper sheets at RT for 1 hour, equol solutions were applied to each zone of the paper (1 drop to each zone). Coloration begins to appear within several minutes and coloration was evaluated visually. The results are shown in table 1. It appeared that the coloration was stronger when the concentration of $HNO_3$ in impregnating solution was higher.

TABLE 1

Impregnation solutions and coloration results

| | | | Coloration depending on Equol concentration | | | |
| --- | --- | --- | --- | --- | --- | --- |
| Exp. | Composition | | 0.5% | 0.12% | 0.05% | 0.01% |
| 1 | 56% $HNO_3$, ml | 0.1 | None | None | None | None |
|  | $H_2O$, ml | 20 | | | | |
|  | $NaNO_3$, g | 5 | | | | |
|  | isoamyl alcohol, ml | 5 | | | | |
| 2 | 56% $HNO_3$, ml | 1 | None | None | None | None |
|  | $H_2O$, ml | 20 | | | | |
|  | $NaNO_3$, g | 5 | | | | |
|  | isoamyl alcohol, ml | 5 | | | | |
| 3 | 56% $HNO_3$, ml | 10 | Pale red | Pale red | Very weak red | None |
|  | $H_2O$, ml | 10 | | | | |
|  | $NaNO_3$, g | 5 | | | | |
|  | isoamyl alcohol, ml | 5 | | | | |
| 4 | 56% $HNO_3$, ml | 20 | Red | Pale red | Very weak red | None |
|  | $H_2O$, ml | 0 | | | | |
|  | $NaNO_3$, g | 5 | | | | |
|  | isoamyl alcohol, ml | 5 | | | | |

Examples 5 to 9

Selectivity of Test Strip Assay

A strip was layered (soaked) with a concentrated solution of nitric acid. The nitric acid solution contained amyl alcohol and sodium hydroxide. The test strip was used for the detection of equol in various samples. Five different samples were prepared as outlined in table 2 below.

TABLE 2

Test samples and results

| Exp. | Sample | Sample production | Result |
|---|---|---|---|
| 5 | 1 | Urine solution mixed out of 10 humans (male, female, age group 20 to 56). No isoflavones have been detected in this sample. | colorless |
| 6 | 2 | Sample 1, with 1% (w/v) multiple vitamins | colorless |
| 7 | 3 | Sample 1, with 1% (w/v) isoflavones | colorless |
| 8 | 4 | Sample 1, with 0.05% (w/v) equol | yellow |
| 9 | 5 | Sample 1, with 0.1% (w/v) equol | orange/red |

Figure 1:
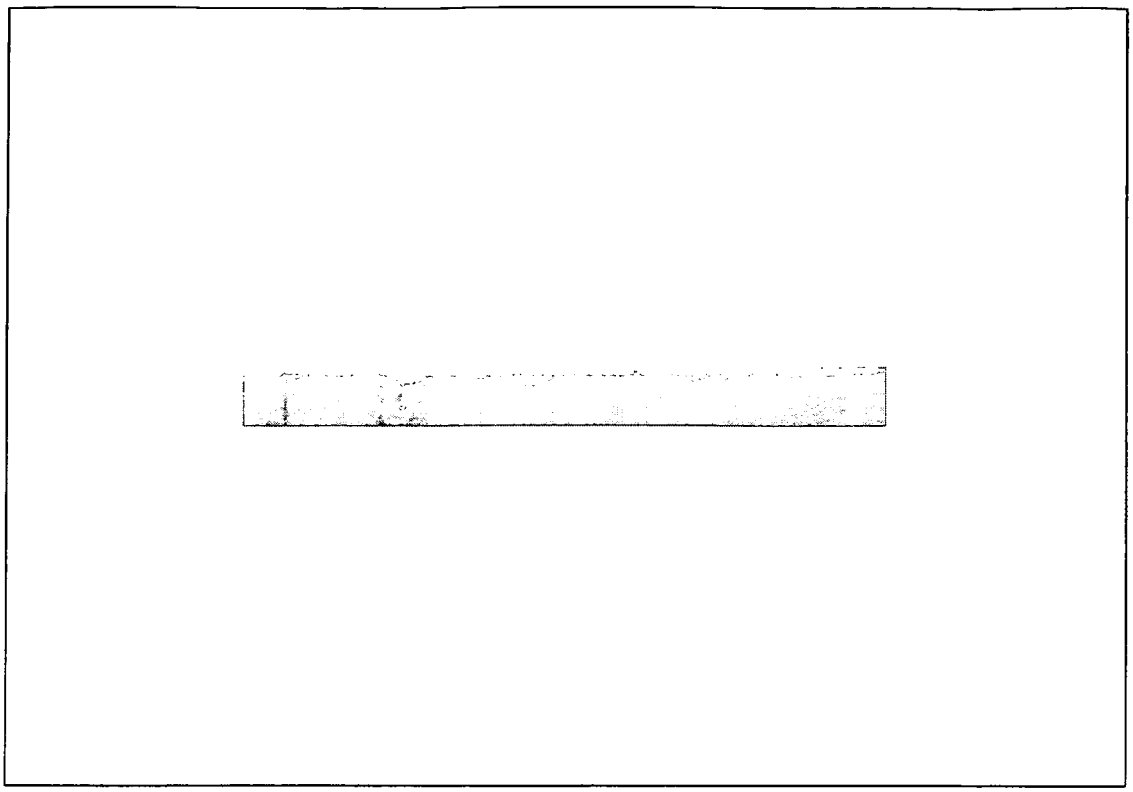
FIG. 1 show a test strip contacted with urine, which does not comprise equol, according to example 5.
Figure 2:
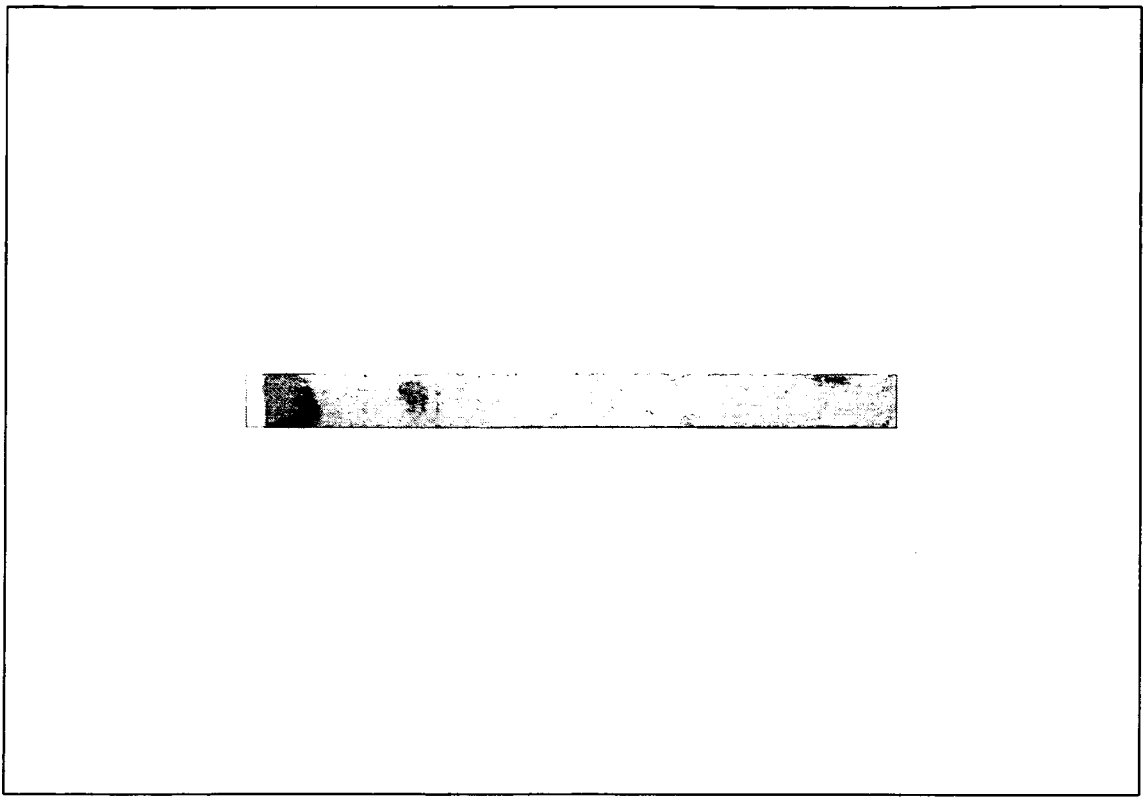
FIG. 2 shows a test strip contacted with urine comprising 0.05% equol according to example 8.
Figure 3:
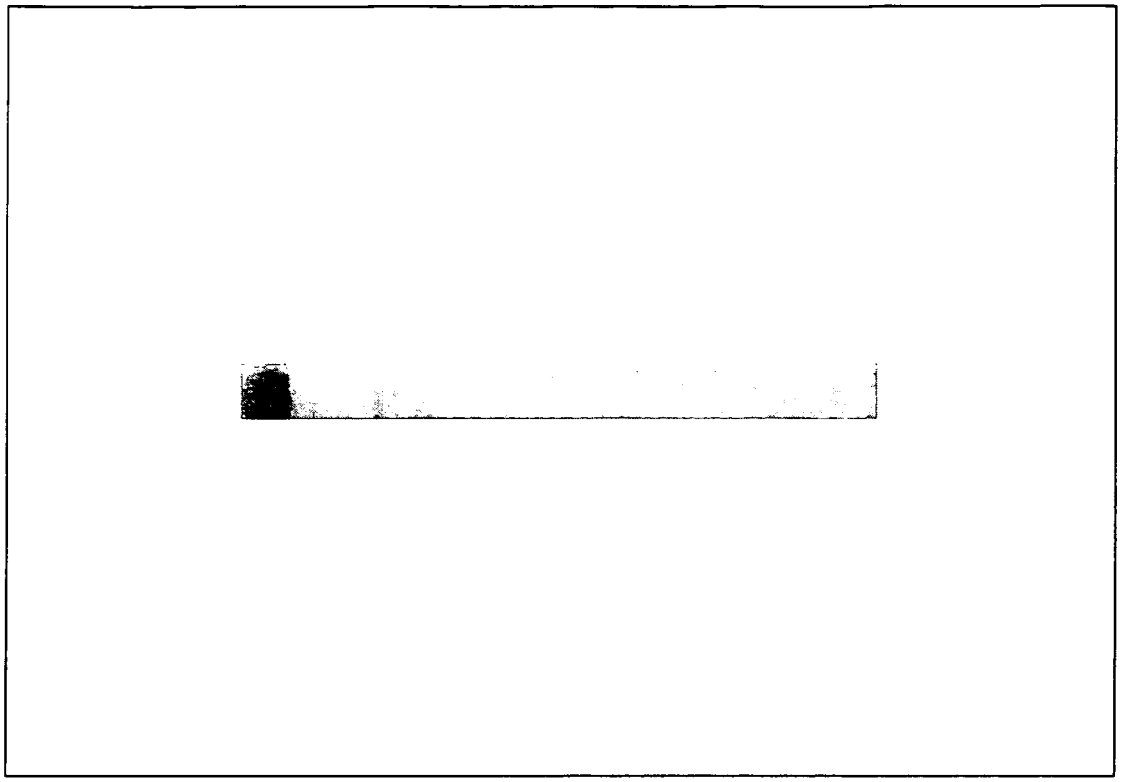
FIG. 3 shows a test strip contacted with urine comprising 0.1% equol according to example 9.

An inventive test strip was dipped into each sample. The color was observed and the results are summarized in table 2 above. Sample 1, which was a blind control, did not show a color reaction. Samples 2 and 3 were additional control samples, which comprised vitamins or mixed isoflavones. They did not show any color reaction either. Sample 4, which comprised 0.05% equol showed a clear color change to strong yellow, with a shade of orange. Sample 5, which comprised 0.1% equol had a strong orange/red color. The color changes could be easily detected with the eye, as shown in FIGS. 1, 2 and 3. The experiments show that the test strip of the invention is applicable for detecting physiological amounts of equol in urine, such as 0.05% or 0.1% (w/v). Such equol concentrations are found in the urine of equol producers after the consumption of daidzein or a daidzein comprising food. Further, the test is highly specific and does not yield false positive results from vitamins, other isoflavones or common urine components.

The invention claimed is:

1. A method for determining whether an aqueous solution comprises equol, wherein the aqueous solution is urine or blood from a person, or a fraction thereof, comprising the steps of (A) contacting the aqueous solution with a test strip for the detection of equol by a color change, wherein the test strip is impregnated with at least one reactive agent for analysing an aqueous solution by contacting the aqueous solution with the strip, wherein the color change occurs when the strip is contacted with an aqueous solution comprising equol, wherein the at least one reactive agent is nitric acid, (B) detecting the presence or absence of a color change, (C) deducing from the presence or absence of the color change whether the solution comprises equol.

2. The method of claim 1, wherein the presence of equol is indicated by a yellow, orange or red color.

3. The method of claim 1, wherein the aqueous solution is unfractionated urine from a person.

4. The method of claim 1, wherein any vitamins, phenols or estrogenic hormones in the aqueous solution do not produce a color change on the test strip.

5. A method for determining whether a person is an equol producer, comprising the steps of (i) contacting urine, blood or a fraction thereof from said person with a test strip for the detection of equol by a color change, wherein the test strip is impregnated with at least one reactive agent for analysing an aqueous solution by contacting the aqueous solution with the strip, wherein the color change occurs when the strip is contacted with an aqueous solution comprising equol, wherein the at least one reactive agent is nitric acid, (ii) detecting the presence or absence of a color change, (iii) deducing from the presence or absence of the color change whether the person is an equol producer.

6. The method of claim 5, wherein before step (i) the person has consumed a predetermined quantity of daidzein or a daidzein-comprising product.

7. The method of claim 5, which comprises contacting unfractionated urine from said person with the test strip.

8. The method of claim 5, wherein any vitamins, phenols or estrogenic hormones in the aqueous solution do not produce a color change on the test strip.

* * * * *